United States Patent [19]

Lech et al.

[11] Patent Number: 5,681,577
[45] Date of Patent: Oct. 28, 1997

[54] MULTIPLE ACTION COLD/SINUS PREPARATIONS

[75] Inventors: Stanley Lech, Rockaway; Alexander M. Schobel, Flemington; John Denick, Jr., Newton, all of N.J.

[73] Assignee: Warner-Lambert Company, Morris Plains, N.J.

[21] Appl. No.: 530,449

[22] Filed: Sep. 19, 1995

Related U.S. Application Data

[63] Continuation of Ser. No. 72,623, Jun. 4, 1993, abandoned.

[51] Int. Cl.$^6$ .............. A61K 47/00; A61K 9/68; A61K 9/28
[52] U.S. Cl. .............. 424/439; 424/440; 424/441; 424/442; 514/979
[58] Field of Search .............. 424/439, 440, 424/441, 442; 514/979

[56] References Cited

U.S. PATENT DOCUMENTS

| | | | |
|---|---|---|---|
| 4,442,086 | 4/1984 | Quinlan | 424/79 |
| 4,461,759 | 7/1984 | Dunn | 424/19 |
| 4,521,401 | 6/1985 | Dunn | 424/19 |
| 4,521,402 | 6/1985 | Dunn | 424/19 |
| 4,522,804 | 6/1985 | Dunn | 424/15 |
| 4,526,777 | 7/1985 | Blume et al. | 424/20 |
| 4,536,511 | 8/1985 | Fischer et al. | 514/404 |
| 4,609,675 | 9/1986 | Franz | 514/568 |
| 4,632,821 | 12/1986 | Peters et al. | 424/15 |
| 4,758,424 | 7/1988 | Denick, Jr. et al. | 424/48 |
| 4,786,508 | 11/1988 | Ghebre-Sellassie et al. | |
| 4,910,023 | 3/1990 | Botzolakis et al. | 424/470 |
| 5,013,716 | 5/1991 | Cherukuri et al. | 514/523 |

FOREIGN PATENT DOCUMENTS

| | | |
|---|---|---|
| 0265226 | 4/1988 | European Pat. Off. |
| 0345787 | 12/1989 | European Pat. Off. |
| 0422290 | 4/1991 | European Pat. Off. |

*Primary Examiner*—Nathan M. Nutter
*Attorney, Agent, or Firm*—Michael J. Atkins; Evan J. Federman

[57] ABSTRACT

A chewable cold/sinus preparation comprising a bitter tasting mixture of a decongestant such as pseudoephedrine and an antihistamine such as diphenhydramine and/or chlorpheniramine maleate is made with no bitter, metallic taste or unpleasant mouthfeel by adsorbing the active drug mixture using a wet granulation process onto a silicon dioxide carrier which comprises from about 50 to about 85% of total weight of the adsorbate composition. A truly multi-symptom relief formula is prepared through the optional addition of an antitussive such as dextromethorphan hydrobromide and/or an analgesic such as meclofenamic acid, aspirin or ibuprofen. Additional excipients such as flavors, sweeteners, lubricants and bulk fillers are added for better taste, improved mouthfeel and as an aid to the tabletting process.

21 Claims, No Drawings

MULTIPLE ACTION COLD/SINUS PREPARATIONS

This is a continuation of copending application Ser. No. 08/072,623 as originally filed on Jun. 4, 1993.

BACKGROUND OF THE INVENTION

There have been numerous efforts over the years to make bad tasting things that are otherwise good for you taste good. This is particularly true in the area of pharmaceuticals where many drugs possess bitter, acidic or metallic tastes. This problem of course, is confined to those drugs which are administered orally and whereas bitter tastes are readily perceived in swallowable tablets or capsules, they are very apparent and unpleasant in chewable delivery systems such as chewable tablets.

The effective taste masking of unpleasant or bitter tasting drugs is important in many respects, not the least of which, particularly in childrens medications, is insuring the likelihood of better patient compliance. Many drugs, both prescription and over-the-counter that are bitter tasting or that possess an undesirable mouth feel can be made less objectionable if they can be encapsulated and swallowed whole with subsequent breakdown and absorption of the active ingredient either in the stomach or enterically in the small intestine. Many drugs however, especially childrens' medications, are better administered in chewable dosage forms since children generally don't like or have difficulty swallowing whole tablets or capsules. Obviously, if the drugs taste bad, chewing the tablet directly exposes the taste buds and sensitive oral tissues to the unpleasant drugs to a greater extent and for a longer period of time thereby exacerbating the problem than if swallowed whole.

There are many known taste masking agents and preparations tailored for specific applications. Sweeteners, flavors, bulking agents and the like have long been used as taste masking agents. See U.S. Pat. No. 5,013,716 to Cherukuri et. al. The general approach is using a composition whose taste is stronger than and thereby overpowers the unpleasant tasting compound. Artificial, high intensity sweeteners have proven particularly useful in this regard.

Fumed silicon dioxide ($SiO_2$) is an ingredient commonly used in the pharmaceutical art as an aid for tablet processing. Very low levels are generally employed however, and the composition is used more as a flow aid than the main carrier material. U.S. Pat. No. 4,526,777 to Blume et. al. discloses the combination of silicon dioxide with microcrystalline cellulose that is useful in tabletting as the two components allegedly provide binding and disintegration functionalities. Syloid®, a micron-sized silica, is also added as a flow enhancer but again, comprised of a fairly low percentage of the overall tablet composition.

U.S. Pat. No. 4,578,424 to Denick et. al. discloses medicament adsorbates consisting of a bitter tasting decongestant and a complex aluminum silicate comprised of silicon dioxide, magnesium oxide and aluminum oxide. The adsorbate can contain up to 30% of the unpleasant tasting drug yet is essentially tasteless when formulated into an ingestible composition.

U.S. Pat. No. 4,910,023 to Botzolakis et. al. discloses a pharmaceutical preparation comprising a poor tasting hygroscopic drug that is taste masked using from about 3.0% to about 30% by weight of silicon dioxide adsorbed onto the drug particle. The pharmaceutical composition is administered as a swallowable capsule or tablet wherein the drug is present in amounts of from 30 to 70% of the total composition.

U.S. Pat. No. 4,786,508 to Ghebre-Sellassie et. al. discloses taste masking of bitter tasting drugs in oral dosage forms using a polymeric coating component that contains a cationic copolymer with residues of (meth)acrylic esters and dimethyl aminoethyl(meth)acrylate. The polymeric coating is salvia-resistant yet acid-soluble for protection in the mouth and buccal area but ingestible once swallowed.

U.S. Pat. No. 4,632,829 to Peters et. al. also teaches a medicament adsorbate where bitter tasting drugs such as the decongestants phenylpropanolamine hydrochloride, pseudoephedrine, phenylephrine hydrochloride and ephedrine are taste-masked by disposing the drug in a complex magnesium trisilicate in flake-like structures that possess a large surface area with multiple interstitial spaces. The absorbate can be administered in any one of a number of carrier dosage forms.

U.S. Pat. No. 4,609,675 to Franz discloses the use of silicon dioxide at low levels as a granulation aid for ibuprofen. U.S. Pat. No. 4,442,086 to Quinlan discloses the use of low levels of silica as a glidant while U.S. Pat. No. 4,356,511 to Fisher teaches the use of silica and cellulose at levels below 1.0% to aid the binding and flow characteristics for wet granulation processing of the drug mazolamine. U.S. Pat. Nos. 4,461,759; 4,522,804; 4,521,402 and '401 all to Dunn disclose the general use of silicon dioxide together with hydrogenated vegetable oil and an acrylic acid polymer as a processing aid.

It is an object of the present invention to provide a novel dual or triple action cold/sinus preparation comprising an unpleasant tasting combination of a decongestant, an antihistamine and optionally, an analgesic pain reliver or cough supressant in a chewable dosage form. More specifically, it is an object of the present invention to provide a pleasant tasting chewable cold/sinus remedy comprising an antihistamine selected form the group comprising diphenhydramine or chlorpheniramine maleate and a decongestant such as pseudoephedrine which not only lack the bitter, metallic taste caused thereby but which imparts a smooth, chewy mouth-feel for easy administration. Optionally, an additional active such as an analgesic or cough supressant may be combined for further symptomatic relief.

SUMMARY OF THE INVENTION

The present invention is an improved chewable cold/sinus medication comprising a decongestant pseudoephedrine, and an antihistamine, such as chlorpheniramine maleate or diphenhydramine hydrochloride. The drugs are incorporated onto an adsorbant material comprising silicon dioxide ($SiO_2$) which surprisingly masks their bitter metallic taste and numbing mouth feel that would otherwise prohibit their use in a chewable tablet dosage form. Additional bitter taste actives such as the antitussive dextromethorphan hydrobromide and the analgesics meclofenamic acid, aspirin, ibuprofen and the like may also be incorporated in the tablet.

DETAILED DESCRIPTION OF THE INVENTION

The combination of two active cold medications provides the present invention with dual action relief not previously made possible in other cold/sinus formulations. Diphenhydramine hydrochloride (−[2-benzhydryloxy)-N,N-dimethylethylamine hydrochloride]) and chlorpheniramine maleate -(4-chlorophenyl)-N,N-dimethyl-2-pyridine propanamine are antihistamines which provide relief to running, watery eyes and congested sinuses by blocking the effects of histamines. Pseudoephedrine hydrochloride (1-phenyl-2-methylaminopanol HCl) is a decongestant which provides systemic relief by dilating and opening clogged or swelled nasal passages for easier breathing. Together, the two active ingredients provide multi-symptom relief not herein before possible.

Optionally, it was also surprisingly and unexpectedly found that a cough supressant such as dextromethorphan hydrobromide (d-3-methoxy-17-methylmorphinan hydrobromide)and/or an analgesic such as meclofenamic acid (2-[(2,6-Dichloro-3-methylphenyl) amino] benzoic acid) could be incorporated into the tablet as well without causing bitter, unpleasant notes while at the same time providing truly multi-functional relief.

Formulation of these ingredients into a chewable tablet, particularly for children's dosage forms is a problem due to the bitter tasting nature of the drugs. Fumed silica or silicon dioxide ($SiO_2$) is a colorless, tasteless amorphous powder that is insoluble in water and acids. These colloidal silica particles are sintered together in chain-like formations that possess surface areas of 50 to 400 $M^2$/gm, depending upon the grade. The pseudoephedrine and diphenhydramine hydrochloride are adsorbed onto the silicon dioxide using a simple, wet granulation process known in the art. The pseudoephedrine and diphenhydramine are first dissolved in water until a clear solution is achieved. Silicon dioxide is then added to a planetary or high-shear mixer (Hobart Co., Saddlebrook, N.J.) and the decongestant/antihistamine solution is subsequently added. After all the ingredients have been blended thoroughly, the mixture is dried in a forced hot air oven. The dried material is then screened and tabletted using standard tablet compression procedures.

Fumed silica, sold under the tradename Cab-o-Sil® (Cabot Corp., Kokoma, Ind.) is comprised of many fine, flake-like structures which when sintered provide a substrate with a large surface area. When the silica powder is mixed with the dissolved drugs, the antihistamine and decongestant can be loaded into or absorbed onto the carrier with relative ease. The fumed silica may comprise from approximately 5 to about 95% by. weight of the entire drug adsorbate preparation. Preferably, the silica will be employed in amounts from about 50 to 90% by weight of the preparation. These high proportionate amounts with respect to the actives have been found to be necessary to both taste-mask the bitter tasting drugs and to provide an acceptable, chewing texture to the tablet during administration of the medicament.

The actives, pseudoephedrine HCl, diphenhydramine HCl or chlorpheniramine maleate are added together in a ratio of from about 30:1 to about 1:30 (decongestant: antihistamine) depending on the dose and can comprise from about 1.0 to about 99% of the total weight of the tablet formulation. Preferably, the decongestant and antihistamine will be combined in a ratio of approximately 1:1 and will comprise from about 15% to about 40% by weight of the total cold/sinus preparation. The optional actives such as the antitussive, dextromethorphan hydrobromide and the analgesics such as meclofenamic acid are also added in similar ratios and preferably would be incorporated in equivalent amounts by weight as the antihistamines and decongestants.

As discussed above, the cold/sinus preparation of the present invention involves adsorbing the active agents onto the fumed silicon dioxide particle by means of a wet granulation process. Preferably other excipients are added as well, particularly when a children's product is prepared. Sodium lauryl sulfate may optionally be added as an excipient which enables the drugs to further penetrate the silica absorbate. Such excipients include lubricants such as magnesium. stearate, binders such as povidone, hydroxymethyl cellulose and starch, waxes such as carnauba and candilillia, buffers such as sodium phosphate or sodium citrate either in combination with their respective acid alone or in combination with other acidulents such as tartaric acid or citric acid etc. Disintegrants such as microcrystalline cellulose and other cellulose derivatives may be added in order to aid in the tabletting and oral administration processes, respectively. Fruit flavors such as grape, cherry, orange, lemon, etc., mint flavors such as spearmint, peppermint and the like and standard flavors such as vanilla or chocolate may all be incorporated to make the taste even more appealable. Food colorings, bulking agents, antioxidants and sweeteners may also added to the mixture prior to tabletting as is known in the art.

The present invention is a multiple relief cold/sinus medication comprising both an antihistamine, a decongestant and optionally an antitussive and/or an analgesic for pain relief in a pleasant, chewable tablet dosage form. Not only must the bitter, metallic taste of the actives diphenhydramine hydrochloride, chlorpheniramine maleate and pseudoephedrine be overcome, but the tablet must also present a smooth, palatable mouth-feel when chewed and swallowed. Without both these functionalities, consumer acceptance and hence, patient compliance in taking the cold/sinus medication especially in children is not likely to any great degree. The problem is of course compounded when additional bitter-tasting actives such as dextromethorphan hydrobromide and meclofenamic acid are added which, without more, further enhance the disagreeable flavor of the present compositions.

The following examples are provided in order to better teach and disclose specific embodiments of the present invention and the manner in which the chewable cold/sinus tablets of the present invention may be prepared. It must be kept in mind that the examples are for illustrative purposes only, and it is recognized that certain variations and changes may be made to alter these formulations in minor degrees. Such variations are still considered to fall within the spirit and scope of the present invention as recited by the claims that follow.

EXAMPLE I

The decongestant/antihistamine adsorbate of the present invention was prepared using the following ingredients in their respective amounts:

|  | Weight | Percent |
| --- | --- | --- |
| 1) Diphenhydramine HCl | 25.0 gms. | 5.0% |
| 2) Pseudoephedrine HCl | 60.0 gms. | 12.0% |
| 3) Cab-o-sil M5 | 415.0 gms. | 83.0% |
| 4) Water | 200.0 gms. |  |
|  | 500.0 gms.* | 100% |

*$H_2O$ not included

The diphenhydramine hydrochloride and pseudoephedrine hydrochloride were mixed in the water until thoroughly dissolved. The Cab-o-sil M5® (silicon dioxide) was poured into a planetary mixer to which the dissolved drug solution is added and mixed at slow speed. This was continued for five (5) minutes until the solution and Cab-o-sil® were completely mixed. The entire composition was dried in a forced hot air oven for seven (7) hours at 50° C. The composition was dried to an LOD of 1.0%. The dried material was then screened through a No. 30 U.S. standard mesh screen and compressed using a conventional tablet hand press into 1.0 gm. tablets, each one possessing a potency of 50 mg. diphenhydramine hydrochloride and 120 mg. pseudoephedrine hydrochloride.

The tablets were then presented to an expert taste panel and chewed in order to determine palatability. None of the samplers expressed detection of the bitter, metallic taste to the extent that would be expected from chewing the drugs and a carrier alone and the tablets were found to impart a smooth, non-chalky texture when chewed which was readily swallowed when mastication was complete.

EXAMPLE II

The decongestant/antihistamine adsorbate of the present invention was prepared using the following ingredients in their respective amounts:

|  | Weight | Percent |
| --- | --- | --- |
| 1) Chlorpheniramine maleate | 3.35 gms. | 0.67% |
| 2) Pseudoephedrine HCl | 100.0 gms. | 20.0% |
| 3) Cab-o-sil MS | 396.65 gms. | 79.33% |
| 4) Water | 200.0 gms. | |
| | 500.0 gms.* | 100% |

*H$_2$O not included

The chlorpheniramine maleate and pseudoephedrine hydrochloride were mixed in the water until thoroughly dissolved. The Cab-o-sil M5® (silicon dioxide) was poured into a planetary mixer to which the dissolved drug solution is added and mixed at slow speed. This was continued for five (5) minutes until the solution and Cab-o-sil® were completely mixed. The adsorbate was dried in a forced hot air oven for five (5) hours to an LOD of less than 2.0%. Magnesium stearate was then added as a lubricant, and tartaric acid was added as an acidulent. The excipients were then thoroughly mixed and the entire composition was compressed using a conventional tablet hand press into 1.0 gm. tablets, each one possessing a potency of 4.0 mg. chlorpheniramine maleate and 120 mg. pseudoephedrine hydrochloride.

Like the formulations of Example I, even without the addition of any flavors or sweeteners the bitter metallic taste of the active ingredients was substantially if not completely reduced.

EXAMPLE III

The chewable cold/sinus preparation in a child's formulation was prepared using the following ingredients.

|  | Weight | Percent |
| --- | --- | --- |
| 1) Diphenhydramine HCl | 12.5 gms. | 1.25% |
| 2) Pseudoephedrine HCl | 30.0 gms. | 3.0% |
| 3) Cab-o-sil® M5 | 207.5 gms. | 20.75% |
| 4) Tartaric Acid | 20.0 gms. | 2.0% |
| 5) Monoammonium glycyrrhizinate | 2.5 gms. | 0.25% |
| 6) Aspartime | 12.0 gms. | 1.20% |
| 7) Purple Lake Coloring | 2.5 gms. | 0.25% |
| 8) Emdex® | 693.5 gms. | 69.35% |
| 9) Magnesium stearate | 7.5 gms. | 0.75% |
| 10) Grape flavor | 12.0 gms. | 1.25% |
| | 1000.00 gms. | 100% |

The pseudoephedrine hydrochloride and diphenhydramine hydrochloride were initially blended in water then added to the Cab-o-sil® as was done in Example I and dried to yield a drug adsorbate of approximately 250 gms. This was then poured into a twin shell blender (Fitzpatrick-Kelly Co., Plainfield, N.J.) and mixed with the Emdex®, a corn syrup bulking agent. The tartaric acid, grape flavor and purple food coloring were then added and the entire composition was mixed for approximately 10 minutes. Monoammonium glycyrrhizinate, a sweetener enhancer and aspartame, a well known high intensity sweetener were then added and mixed for an additional five (5) minutes. Finally, magnesium stearate, a lubricant, was added in order to aid in the tabletting process. Mixing continued for an additional three (3) minutes. Once the components were thoroughly blended, the mixture was discharged from the blender and again compressed into 1.0 gm. tablets using standard tabletting compression equipment as before. The chewy grape flavored tablets were evaluated by a taste panel and were found to possess and excellent, up-front grape taste with no unpleasant or bitter aftertaste and a smooth, non-chalky texture. Such tablets afford the patient a dose of 12.5 mg. diphenhydramine hydrochloride and 30.0 mg. pseudoephedrine.

EXAMPLE IV

A decongestant/antihistamine/antitussive adsorbate of the present invention was made using the following ingredients in their respective amounts:

|  | Weight | Percent |
| --- | --- | --- |
| 1) Chlorpheniramine maleate | 8.0 gms. | 0.80% |
| 2) Pseudoephedrine HCl | 120.0 gms. | 12.0% |
| 3) Dextromethorphan HBr | 60.0 gms. | 6.0% |
| 4) Cab-o-sil® M5 | 812.0 gms. | 81.2% |
| 5) Water | 200.0 gms. | |
| | 1000.0 gms.* | 100% |

*H$_2$O not included

The chlorpheniramine maleate dextromethrophan HBr and pseudoephedrine hydrochloride were mixed in the water until throughly dissolved. The Cab-o-sil® M5 (silicone dioxide was poured into a planetary mixer to which the dissolved drug solution is added and mixed at slow speed. This was continued for five (5) minutes until the solution and Cab-o-sil® were completely mixed. The entire composition was dried in a forced hot air oven for seven (7) hours at 50° C. The composition was dried to an LOD of 1.25%. The dried material was then screened through a No. 30 U.S. standard mesh screen. The excipients were added as mentioned before and the blend was compressed using a conventional tablet hand press into 1.0 gm. tablets, each one possessing a potency of 4 mg. chlorpheniramine maleate and 60 mg. pseudoephedrine hydrochloride and 30 mg. dextromethorphan HBr.

The tablets then presented to an expert taste panel and chewed in order to determine palatability. None of the samplers expressed detection of a bitter, metallic taste to any substantial degree an the tablets were found to impart a smooth, non-chalky texture when chewed which was readily swallowed when mastication was complete.

What we claim is:

1. A multi-relief, chewable cold/sinus preparation with little to no objectionable taste comprising an effective amount of a bitter tasting mixture of active ingredients comprising an antihistamine and a decongestant in a carrier consisting essentially of silicon dioxide.

2. The cold/sinus preparation of claim 1 wherein said decongestant is selected from the group consisting of pseudoephedrine.

3. The cold/sinus preparation of claim 2 wherein said antihistamine is selected from the group consisting of diphenhydramine, chlorpheniramine maleate and mixtures thereof.

4. The chewable cold/sinus preparation of claim 3 wherein said silicon dioxide is present in an amount of from about 5% to about 95% by weight of the entire cold/sinus preparation.

5. The chewable cold/sinus preparation of claim 4 wherein said silicon dioxide is present in an amount of from about 50% to about 95% by weight of the adsorbate preparation.

6. The chewable cold/sinus preparation of claim 5 wherein said decongestant and said antihistamine are combined in ratio of from about 30:1 to about 1:30, respectively.

7. The cold/sinus preparation of claim 6 wherein said decongestant and said antihistamine are combined in a ratio of from about 1:3 to about 3:1.

8. The cold/sinus preparation of claim 7 wherein said pseudoephedrine and said diphenhydramine or chlorpheniramine maleate comprise from about 1% to about 90% by weight of the entire composition.

9. The cold/sinus preparation of claim 8 wherein said pseudoephedrine and said diphenhydramine or chlorpheniramine maleate comprise form about 15% to about 40% by weight of the entire composition.

10. The cold/sinus preparation of claim 9 wherein said diphenhydramine and pseudoephedrine are the hydrochloride salts thereof.

11. The cold/sinus preparation of claim 10 wherein said pseudoephedrine, diphenhydramine and said chlorpheniramine maleate are adsorbed onto the silicon dioxide material.

12. The cold/sinus preparation of claim 11 further comprising an antitussive.

13. The cold/sinus preparation of claim 12 wherein said antitussive is selected from the group consisting of dextromethorphan hydrobromide.

14. The cold/sinus preparation of claim 13 further comprising an analgesic pain relief composition.

15. The cold/sinus preparation of claim 14 wherein said analgesic is selected from the group consisting of meclofenamic acid, ibuprofen, aspirin and mixtures thereof.

16. The cold/sinus preparation of claim 15 further comprising flavors, sweeteners, anti-caking agents, tabletting agents, stabilizers, granulation agents and mixtures thereof.

17. The cold/sinus preparation of claim 16 prepared as a chewable tablet.

18. The cold/sinus preparation of claim 17 wherein said tabletting agent is selected from the group consisting of microcrystalline cellulose, hydroxypropyl cellulose, other cellulose derivatives, sucrose, mannitol, lactitol, sorbitol, maltitol and mixtures thereof.

19. The cold/sinus preparation of claim 18 wherein said flavor is selected from the group consisting of fruit flavors, mint flavors, vanilla, chocolate and mixtures thereof.

20. The cold/sinus preparation of clam 19 wherein said granulation agent is selected from the group consisting of povidone, high fructose corn syrup, cellulose derivatives and mixtures thereof.

21. A method for the treatment of colds and sinus discomfort comprising the oral administration of the chewable tablet of claims 1, 9, 12 or 16.

* * * * *